United States Patent [19]

Ong

[11] Patent Number: 4,633,879
[45] Date of Patent: Jan. 6, 1987

[54] ELECTRODE WITH DISPOSABLE INTERFACE MEMBER

[75] Inventor: Lincoln Ong, Minnetonka, Minn.

[73] Assignee: Lec Tec Corporation, Minnetonka, Minn.

[21] Appl. No.: 94,821

[22] Filed: Nov. 16, 1979

[51] Int. Cl.$^4$ ............................ A61B 5/04; A61N 1/04
[52] U.S. Cl. ................................ 128/641; 128/303.13; 128/798
[58] Field of Search ................................ 128/639–641, 128/644, 303.13, 983, 798, 802, 803; 604/20

[56] References Cited

U.S. PATENT DOCUMENTS

| | | | |
|---|---|---|---|
| 1,989,282 | 1/1935 | Kimble et al. | 128/798 |
| 3,911,906 | 10/1975 | Reinhold, Jr. | 128/641 |
| 3,993,049 | 11/1976 | Kater | 128/641 X |
| 3,998,215 | 12/1976 | Anderson et al. | 128/641 |
| 4,066,078 | 1/1978 | Berg | 128/641 |
| 4,088,133 | 5/1978 | Twentier | 128/644 X |
| 4,125,110 | 11/1978 | Hymes | 128/641 |
| 4,458,696 | 7/1984 | Larimore | 128/798 |

FOREIGN PATENT DOCUMENTS 2814061 10/1978 Fed. Rep. of Germany ........................ 128/303.13
2045088 10/1980 United Kingdom ................ 128/798

*Primary Examiner*—Lee S. Cohen
*Attorney, Agent, or Firm*—Robert W. Doyle

[57] ABSTRACT

An electrode for epidermical use for stimulation, iontophoresis, monitoring and grounding electrical contact applications to the skin may be provided having a self-adhesive, disposable, skin interface portion and a non-disposable backer portion, which is easily strippable from the skin interface portion; whereof the interface portion may be a cohesive and electrically conductive material having adhesive properties and the backer portion may be a durable, flexible and resilient material to which the interface portion may normally be adhered and through which an electrical connection may be made to the interface portion, the backer portion and interface portion being cleanly strippable from one another after use.

8 Claims, 5 Drawing Figures

U.S. Patent  Jan. 6, 1987  4,633,879

ELECTRODE WITH DISPOSABLE INTERFACE MEMBER

BACKGROUND OF THE INVENTION

This invention relates to medical EKG and EMG electrodes, and more specifically relates to those types of electrodes used on the skin which are self adhering without the use of tape or other auxiliary securing means. Berg, U.S. Pat. No. 4,066,078, and Hymes, U.S. Pat. No. 4,125,110 have disclosed monitoring and stimulation electrodes of this type. Berg teaches a sheet of complex organic polymer plasticized with a polyhydric alcohol as a skin interface member. Hymes teaches a sheet of high molecular weight hydrophilic polysaccharide material (karaya gum et al.), containing an electrolytic salt, water and alcohol, as a skin interface member.

Both Berg and Hymes teach an electrically conductive current distribution backer member containing a snap connector type electrical connector for mating with an electrical lead wire. These backer members have been taught principally to be of aluminum foil, or a structural and electrical equivalent or substitute for aluminum foil, such as metallic foils, conductive polymers, graphitized or metallized cloth or wire mesh.

These type backer members while taught to be pliable and sufficiently strong to support the snap connector, are not reusable. They are themselves electrically conductive. Moreover, they are taught to be pliable whereby they are easily mechanically workable beyond their elastic limit to conform to many shapes. These prior art electrodes have designed into them a certain desired amount of "softness" and lack of resilience which permits the backer member to conform to the skin surface. While this is a desirable feature it does not lend itself to a durable backer member which can be reusable and from which the interface member can be easily stripped.

In an effort to reduce ever increasing medical costs, it is desirable to have a disposable self adherent electrode where a part of the electrode is reusable. Moreover, it is desirable to provide such an electrode where the backer member is electrically non-conductive permitting a touching thereof without an electrical shock hazzard.

An object of this invention is to provide an electrode having a disposable, adhesive, electrically conductive skin interfacing member which is strippable from a non-disposable, electrical-connection, backer member.

Another object of this invention is to provide this electrode with a backer member which provides a means for making an electrical connection to the skin interfacing member, this backer member itself being electrically non-conductive.

A further object of this invention is to provide such a backer member of durable, flexible and resilient material, the adhesive skin interface member adhering thereto while also being cleanly strippable therefrom.

An even further object of this invention is to provide such a backer member with reinforcement, this surface being sufficiently rough to promote adherence of the skin interface portion while sufficiently smooth to allow release for clean strippability.

SUMMARY OF THE INVENTION

The objects of this invention may be realized in a medical electrode for epidermical use having an electrically conductive, non-liquid, self-adhesive, disposable skin interfacing member and a non-disposable backer member from which the skin interfacing member may be easily and cleanly stripped by peeling it away.

The electrically conductive interfacing member may be a single, flat, cohesive sheet of material cut into a rectangular or other desirable shape. This sheet may pressure adhere to the backer member and may have a protective peel-off covering placed on its other side.

The backer member may be a sheet or film of plastic or other material having good peel-release characteristics while providing a surface to which the interfacing member may securedly adhered while in normal use. This backer sheet may be reinforced with rayon, nylon, cotton or other types of thread which may leave it with a corrugated-like or "bumpy" surface facilitating the adhesion of the interfacing member.

A conductive snap connector may be secured through the backer member sheet and may extend outwardly away from the 15 backer to interface sheet union.

DESCRIPTION OF THE DRAWINGS

The novel structure, features and advantages of this invention will be readily understood from a reading of the following detailed description of the invention in conjunction with the attached drawings in which like numerals refer to like elements, and wherein.

DETAILED DESCRIPTION OF THE INVENTION

Figure 1:
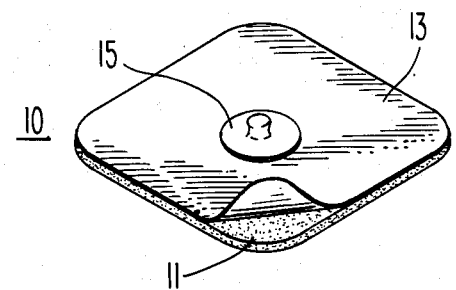
FIG. 1 is a perspective view of the electrode invention showing the backer member and interface sheet partially stripped away from one another.

A medical electrode 10, FIG. 1, for stimulation, iontophoresis, grounding and monitoring uses to the skin of the patient has a disposable skin interface member 11, FIG. 1, and a non-disposable backer member 13 containing an electrical connector 15.

Figure 2:
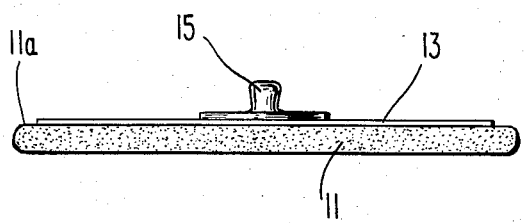
FIG. 2 is a side elevation of the electrode showing the interface sheet, the backer member and the electrical snap connector in the assembled state.

Interfacing member 11 is a sheet of adhesive and electrically conductive material, which has been shaped into a uniformly thick sheet as seen in FIG. 2.

This interfacing sheet 11 can be made from a number of materials including an electrically conductive sheet of complex organic polymer plasticized with a polyhydric alcohol, as taught by Berg, U.S. Pat. No. 4,006,078, or a sheet of high molecular weight hydrophylic polysaccahride material, containing an electrolytic salt, water and alcohol, as disclosed by Hymes, U.S. Pat. No. 4,125,110, or any substitute or equivalent therefor which exhibits desirable "flow" characteristics while remaining a tacky cohesive substance capable of good electrical conductivity.

This interfacing sheet 11 can be cut to any shape that is desired and quite typically is of a rectangular shape as shown in the FIGS. 1, 2. The thickness of this interfacing sheet 11 is uniform throughout. However, this uniform sheet can be of any of various thicknesses. A range of 0.015 to 0.25 inches is common. With a lesser thicknesses, the interfacing sheet 11 is a film which coats the surface of the backer member 13 to its edges. With greater thicknesses, the interfacing sheet 11 is a self supporting sheet which can extend beyond the edges of the backer member 13 allowing for a protruding surface 11a, FIG. 2, by which the interface sheet 11 can begin to be peeled away from the backer member 13.

An electrically conductive snap connector 15 is secured through the backer member 13 to make physical contact with the electrically conductive interfacing sheet 11. This snap connector 15 can be placed anywhere along the surface of the backer member 13 so long as it is placed in direct electrical contact with the interfacing sheet 11. The snap connector 15 can be made of any suitable electrically conductive material such as stainless steel, silver or silver chloride coated material, or carbonized rubber or carbonized polycarbonate. As long as the snap connector 15 acts to provide a good electrical connection between an electrical lead connectable thereto and the electrically conductive interfacing sheet 11, any number of suitable materials may be used in constructing that connector 15.

The backer member 13 is a relatively thin sheet of material cut to the shape of the interface member 11. As stated above, in some instances the dimensions of this backer sheet 13 will be the same as the interface sheet 11 and in other instances will be slightly smaller than the interface sheet 11. The backer sheet 13 is made of a tough, durable, flexible yet resilient material which will return to original shape, including configurations of reinforced vinyl, reinforced Dupont Mylar ® brand polyester film, reinforced paper or polyethylene, polyester materials.

Figure 3A:
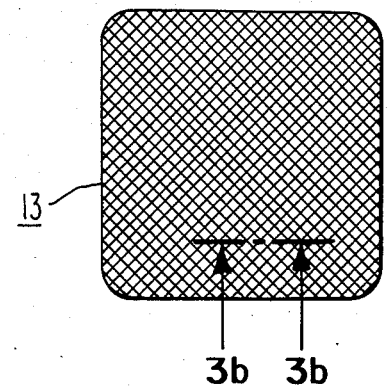
FIG. 3a shows a top elevation view of the reinforced plastic backer member embodiment before the assembly of the electrode.
Figure 4:
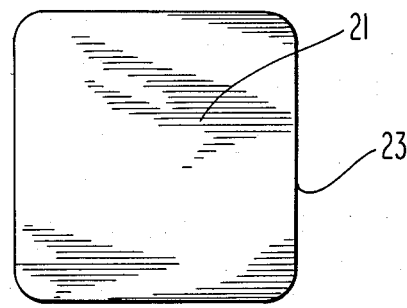
FIG. 4 shows a top elevation view of the plastic and paper sandwich embodiment for the backer member.

FIGS. 3a and 4 show two embodiments for this backer 13. FIG. 3a shows a plastic sheet with reinforced mesh material therein, while FIG. 4 shows a paper sheet reinforced with a plastic film on one side.

Figure 3B:
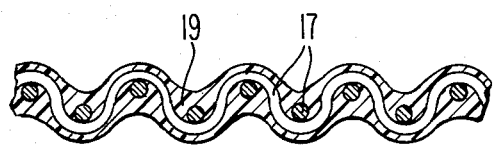
FIG. 3b shows a sectional view of the reinforced plastic backer member of FIG. 3a, in cross section showing the plastic sheet with woven reinforcement within the plastic sheet.

The embodiment of FIG. 3a, has a woven mesh 17 of rayon, nylon, dacron or cotton strands, FIG. 3b, which is used as reinforcement for plastic sheeting 19 of vinyl, Dupont Mylar ® brand polyester film, or polyethylene or similar material. This reinforcement mesh 17, an open weave material, has a mesh size, holes per inch, providing stretch characteristics. This mesh material has a thickness of from 0.025 to 0.05 inches and reinforces 0.001 to 0.015 inches thick plastic film 19. The combination results in a relatively smooth surface, in microspect, from which the interface sheet 11 can be cleanly stripped, by peeling away, without leaving a residual. The mesh reinforcement 17, however, as it has a thickness greater than the film 19 raises the surface of the film 19 and adds a certain roughness or "bumps", in macrospect, which are characterized by minute, smooth surface depressions between strands, whereby the openings in the woven mesh material 17 have been filled with plastic film 19. The reinforced plastic sheet 13, FIG. 3a, therefore provides a plurality of shallow, minute depressions in the backer sheet's 13 surface into which the interfacing sheet 11 may "flow" facilitating a stronger bond between the interfacing member sheet 11 and the backer member sheet 13 by adding a mechanical locking force which with the adhesiveness is sufficient to maintain the electrode 10 intact during ordinary use. This electrode 10 can be applied and removed from a patient's skin without coming apart.

The snap connector 15 when applied to the backer sheet 13 normally does not take up more than 25% of the backer surface, quite often less than 10%. The underside of the snap connector 15 makes direct electrical connection to the interfacing sheet 11 when the electrode 10 is assembled.

As alternative to the mesh reinforced plastic film, FIGS. 3a, 3b, a paper reinforced plastic sheet, FIG. 4, may be used. A thin film of vinyl or Dupont Mylar ® brand polyester film 21, 0.001 to 0.005 inches thick, is thermally bonded to a sheet of paper 23, 0.005 to 0.015 inches thick. The paper side 23 of this backer member 13 forms the outside of the electrode while the plastic coated side 21 contacts the interfacing sheet 11. The connector 15 stands out from the paper side 23 when the electrode 10 is assembled.

The electrode 10 can include a peel-off protective covering for protecting the interfacing member 11 during storage. With this protective covering removed, the electrode 10 can be applied directly to the skin of a patient.

Following a period of use, after a determination that the electrode 10 has become stale (i.e., the interfacing sheet 11 has degredated), or upon conclusion of use, the electrode 10 is removed from the skin of the patient.

After removal, the interfacing sheet 11 can be peeledaway from the backer 13 and discarded. The backer 13 including its electrical connector 15 are saved. A fresh sheet of interfacing material 11 may then be pressed against the backer 13 to form a new electrode 10. Excessive interfacing material 11 may be trimmed away to form a neat structure.

The present invention provides for a reusable electrode having a reusable backer sheet 13 which can withstand many strippings without tearing or losing its shape and which is capable of being returned to its original shape once stripped of the interfacing sheet 11. An electrical connector 15 is permanently attached to the backer 13. Both the interface member 11 and the backer 13 are pliable materials which easily mold to the skin surface and are easily peeled back. The backer member 13 is resilient and tends to hold its original shape while the interface member 11 is completely pliable.

The invention provides the advantage of using fresh interfacing material 11 for each electrode application and for each patient while disposing of a minimum amount of structure. The backer sheet 13 and connector 15 can be salvaged thereby reducing the cost of materials. This cost of materials can be substantial in hospital operations where a large number of disposable electrodes are normally used or in the outpatient situation where stimulation, pain control, or monitoring functions are performed necessitating the use of a large number of disposable electrodes.

It is important that the surface of the backer 13 presents a structure for relatively significant adhesion by the interfacing sheet 11 which facilitates the electrode 10 assembly remaining intact during ordinary use. A clean release is important and facilitated by having the cohesive forces of the interfacing sheet 11 exceed the adhesiveness when that interfacing sheet 11 is peeled-away, i.e., it is subjected to a combination of tensional and shear forces concentrated in a line and propagated across the sheet 11 in a wave fashion. It is equally important that the backer 13 be rugged enough to withstand repeated strippings and resilient to return to shape once stripped.

Many changes can be made in the above-described electrode structure without departing from the intent and scope thereof. Modifications can be made which are within the scope of the present-invention. As an example, the backer sheet 13 embodiment shown in FIGS. 3a, 3b, need not include the reinforcement woven thread mesh 17. The plastic sheet 13 may be molded from a single piece of plastic with larger thickness and thinner thickness. Specifically, the reinforcement woven mesh 17 of rayon, etc, threads imbeded in the plastic sheet 19 may be replaced by thicker sections of plastic formed as part of the sheet 13 from the film 19 is a rectangular grid similar to the grid pattern created by the reinforcing mesh 17 seen from FIG. 3a. The larger thickness of plastic cross section would act as reinforcement to the thinner web sections. A backer 13 produced in this manner would have minute rectangular depressions in the surface of the plastic sheet just as the first embodiment described above in connection with FIGS. 3a, 3b. It is intended, therefore, that all matter contained in the above description and shown in the accompanying drawings be interpreted as illustrative and not be taken in the limiting sense.

What is claimed is:

1. A partially reuseable medical electrode comprising:

adhesive electrical interfacing means for making an electrical connection to the skin surface during electrode use;

electrical connector means for making an electrical connection; and non-conductive durable backer means for releasable adherence to the interlacing, said electrical connector means secured to and extending through said backer means for making an electrical connection between said secured electrical connector means and said electrical interfacing means when said electrical interfacing means is adhered to said backer means, said backer means fabricated of a tough, flexible, but resilient material being capable of repeated clean strippings of said electrical interfacing means from said backer means, and said backer means returning to original shape after each such stripping allowing reuse of said backer means, and allowing reuse of said electrical connector means secured to said backer means.

2. The electrode of claim 1 wherein said backer means is a sheet of non-conductive paper with a sheet plastic reinforcement bonded to one side thereof, said paper being on the outside away from said electrical interfacing means.

3. The electrode of claim 1 wherein said backer means is a sheet of plastic leaving minute depressions in the surface thereof engaging said electrical interfacing means.

4. The electrode of claim 3 wherein said backer means is reinforced with mesh therewithin.

5. The electrode of claim 4 wherein said plastic is nonconductive and covers said mesh to form a continuous sheet.

6. The electrode of claim 5 wherein said mesh thickness is greater than said plastic film thickness.

7. The electrode of claim 6 wherein said mesh thickness creates said minute depressions wherein said depressions are smooth shallow depressions in the surface of said backer means.

8. The electrode of claim 7 wherein said interfacing means flows into said shallow depressions in said backer means when pressed thereagainst facilitating said adhesion of said interfacing means to said backer means.

* * * * *